(12) United States Patent
Shimoda et al.

(10) Patent No.: US 11,191,507 B2
(45) Date of Patent: Dec. 7, 2021

(54) BONE DENSITY MEASUREMENT DEVICE, BONE DENSITY MEASUREMENT SYSTEM, AND IMAGING ASSISTING TOOL

(71) Applicant: MEDIA CO., LTD., Tokyo (JP)

(72) Inventors: Shinji Shimoda, Kanagawa (JP); Kaoru Kobayashi, Kanagawa (JP); Akitoshi Katsumata, Gifu (JP); Hironobu Tsuji, Tokyo (JP); Yosuke Tsuji, Tokyo (JP); Tatsuro Hayashi, Tokyo (JP)

(73) Assignee: MEDIA CO., LTD., Tokyo (JP)

( * ) Notice: Subject to any disclaimer, the term of this patent is extended or adjusted under 35 U.S.C. 154(b) by 0 days.

(21) Appl. No.: 16/477,170

(22) PCT Filed: Jan. 10, 2018

(86) PCT No.: PCT/JP2018/000357
§ 371 (c)(1),
(2) Date: Jul. 10, 2019

(87) PCT Pub. No.: WO2018/131611
PCT Pub. Date: Jul. 19, 2018

(65) Prior Publication Data
US 2019/0343475 A1    Nov. 14, 2019

(30) Foreign Application Priority Data
Jan. 10, 2017 (JP) .............. JP2017-002038

(51) Int. Cl.
*A61B 6/14* (2006.01)
*A61B 6/00* (2006.01)

(52) U.S. Cl.
CPC ............ *A61B 6/5217* (2013.01); *A61B 6/145* (2013.01); *A61B 6/469* (2013.01); *A61B 6/505* (2013.01); *A61B 6/583* (2013.01)

(58) Field of Classification Search
None
See application file for complete search history.

(56) References Cited

U.S. PATENT DOCUMENTS 4,941,164 A * 7/1990 Schuller .................. A61B 6/14
378/162
6,246,745 B1 * 6/2001 Bi .......................... A61B 6/465
378/54
(Continued)

FOREIGN PATENT DOCUMENTS

EP    1649809 A1    4/2006
JP    62266053 A    11/1987
(Continued)

OTHER PUBLICATIONS

International Search Report dated Mar. 13, 2018 issued to corresponding PCT Application No. PCT/JP2018/000357.
(Continued)

*Primary Examiner* — Thomas R Artman
(74) *Attorney, Agent, or Firm* — Manatt, Phelps & Phillips, LLP

(57) ABSTRACT

Provided are: a device (1) and a system (100) for quantitatively calculating bone density by using an X-ray image of a bone pail, in particular, an alveolar bone; and an imaging assisting tool (4) for accurately and easily performing X-ray imaging of an alveolar bone. This bone density measurement device (1) comprises: an image display unit (101) for displaying X-ray images for an imaged bone part and a reference body on the same screen; a reference body density measurement unit (103) for measuring the density of the displayed X-ray image for the reference body; a bone part density measurement unit (105) for measuring the density of the displayed X-ray image for the bone part; and a bone density calculation unit (106) for calculating the hone den-
(Continued)

sity of the bone part by comparing the density of the X-ray image for the bone part with the density of the X-ray image for the reference body.

10 Claims, 19 Drawing Sheets

(56) References Cited

U.S. PATENT DOCUMENTS

| | | | |
|---|---|---|---|
| 7,050,534 B2* | 5/2006 | Lang | G03B 42/02 378/54 |
| 7,058,159 B2* | 6/2006 | Lang | A61B 6/505 378/54 |
| 7,245,697 B2* | 7/2007 | Lang | A61B 6/505 378/54 |
| 7,292,674 B2* | 11/2007 | Lang | G03B 42/02 378/54 |
| 7,379,529 B2* | 5/2008 | Lang | A61B 6/505 378/54 |
| 7,488,109 B2* | 2/2009 | Hangartner | A61B 6/4035 378/168 |
| 7,599,468 B2* | 10/2009 | Zuendorf | A61B 6/505 378/38 |
| 7,676,023 B2* | 3/2010 | Lang | G06T 7/0012 378/54 |
| 7,995,822 B2* | 8/2011 | Lang | A61B 5/4509 382/128 |
| 8,007,171 B2* | 8/2011 | Lee | G06T 7/0012 378/169 |
| 8,031,836 B2* | 10/2011 | Lang | A61B 6/563 378/54 |
| 8,260,018 B2* | 9/2012 | Lang | A61B 6/469 382/128 |
| 8,320,654 B2* | 11/2012 | Takaishi | A61B 6/583 382/132 |
| 8,649,481 B2* | 2/2014 | Lang | A61B 6/583 378/54 |
| 8,781,191 B2* | 7/2014 | Lang | G09B 23/30 382/128 |
| 9,155,501 B2* | 10/2015 | Lang | A61B 6/505 |
| 10,507,003 B2* | 12/2019 | Uber, III | G01R 33/481 |
| 2003/0031292 A1* | 2/2003 | Lang | A61B 6/583 378/54 |
| 2003/0063704 A1* | 4/2003 | Lang | A61B 6/563 378/54 |
| 2005/0010106 A1* | 1/2005 | Lang | A61B 6/469 600/425 |
| 2005/0226374 A1* | 10/2005 | Lang | A61B 6/508 378/54 |
| 2006/0210018 A1* | 9/2006 | Lang | A61B 6/563 378/54 |
| 2007/0025607 A1 | 2/2007 | Takaishi | |
| 2007/0133739 A1* | 6/2007 | Hangartner | A61B 6/583 378/54 |
| 2007/0274444 A1* | 11/2007 | Lang | G03B 42/02 378/54 |
| 2008/0219412 A1* | 9/2008 | Lang | A61B 6/563 378/207 |
| 2008/0253506 A1* | 10/2008 | Zuendorf | A61B 6/583 378/18 |
| 2009/0225958 A1* | 9/2009 | Lang | A61B 6/505 378/207 |
| 2010/0098212 A1* | 4/2010 | Lang | G06T 7/0012 378/54 |
| 2010/0130832 A1* | 5/2010 | Lang | G06T 7/11 600/300 |
| 2012/0027283 A1* | 2/2012 | Lang | A61B 6/4423 382/132 |
| 2012/0087468 A1* | 4/2012 | Lang | A61B 6/505 378/56 |
| 2013/0039592 A1* | 2/2013 | Lang | A61B 6/469 382/232 |
| 2014/0153810 A1* | 6/2014 | Lang | A61B 6/14 382/132 |
| 2015/0003712 A1* | 1/2015 | Lang | A61B 6/583 382/132 |
| 2016/0128659 A1 | 5/2016 | Carton et al. | |
| 2016/0253797 A1* | 9/2016 | Lang | A61B 6/469 382/132 |
| 2018/0242944 A1* | 8/2018 | Uber, III | A61B 5/0035 |
| 2019/0343475 A1* | 11/2019 | Shimoda | A61B 6/14 |
| 2020/0146647 A1* | 5/2020 | Uber, III | G01R 33/481 |

FOREIGN PATENT DOCUMENTS

| | | |
|---|---|---|
| JP | 3300690 B2 | 7/2002 |
| JP | 2004174162 A | 6/2004 |
| JP | 2007136213 A | 6/2007 |
| JP | 4077430 B2 | 4/2008 |
| JP | 2016523162 A | 8/2016 |

OTHER PUBLICATIONS

Written Opinion dated Mar. 13, 2018 issued to corresponding PCT Application No. PCT/JP2018/000357.

* cited by examiner

[FIG.1]
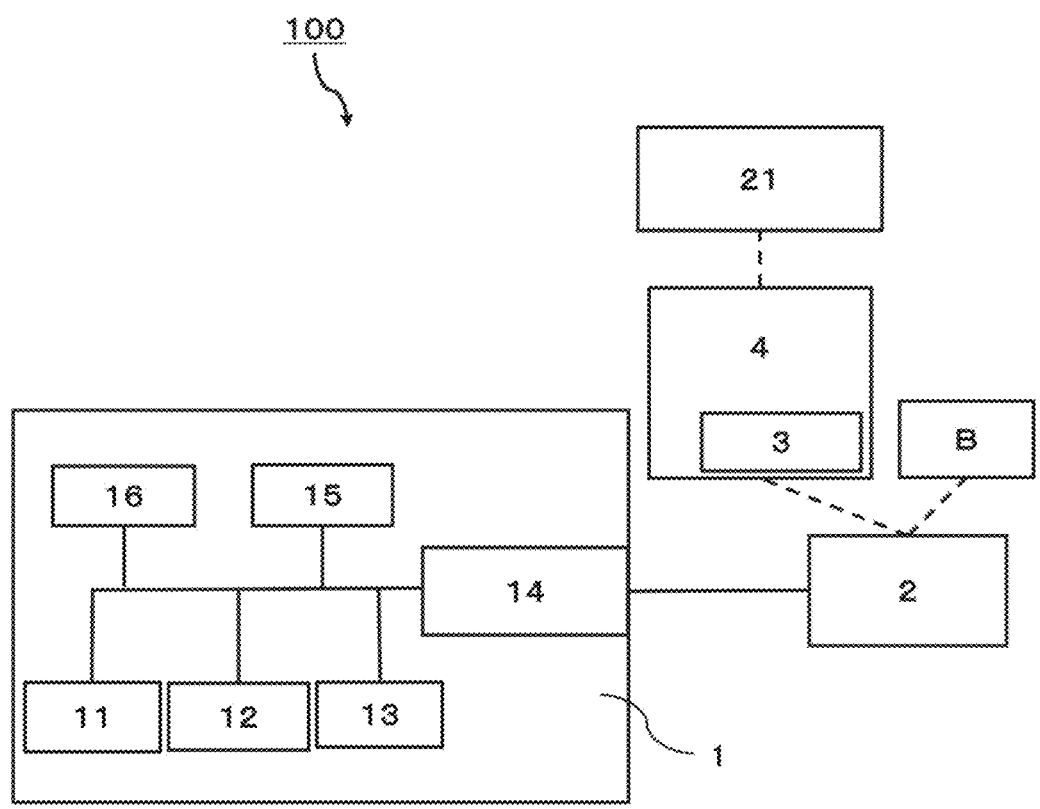

[FIG.2]
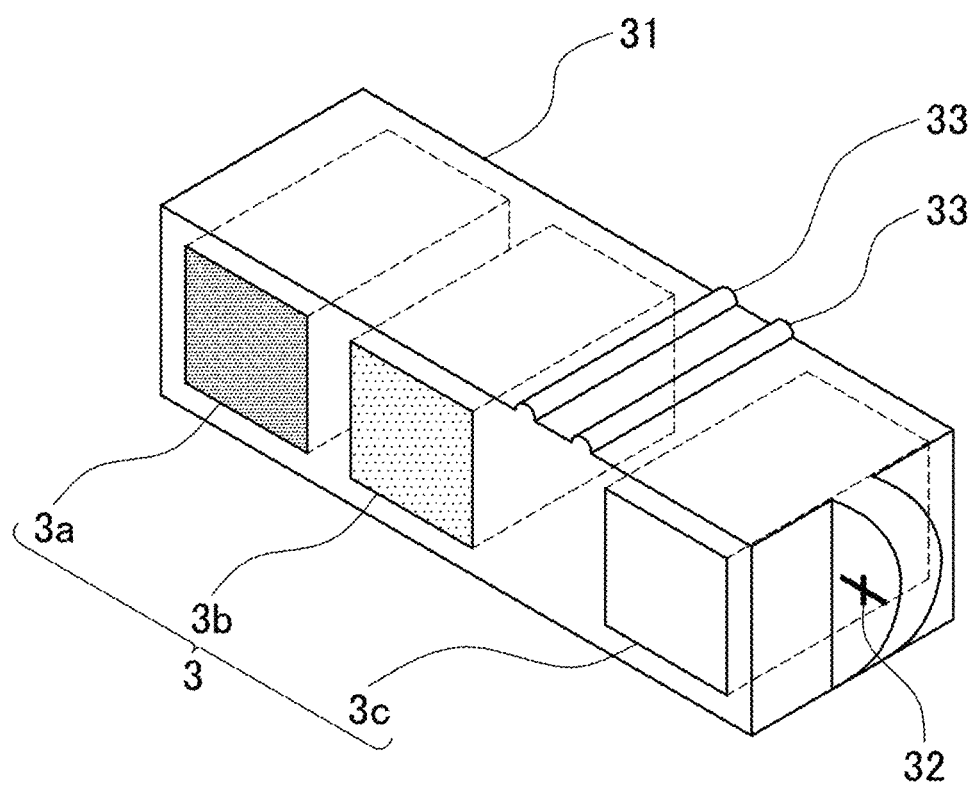

[FIG.3]
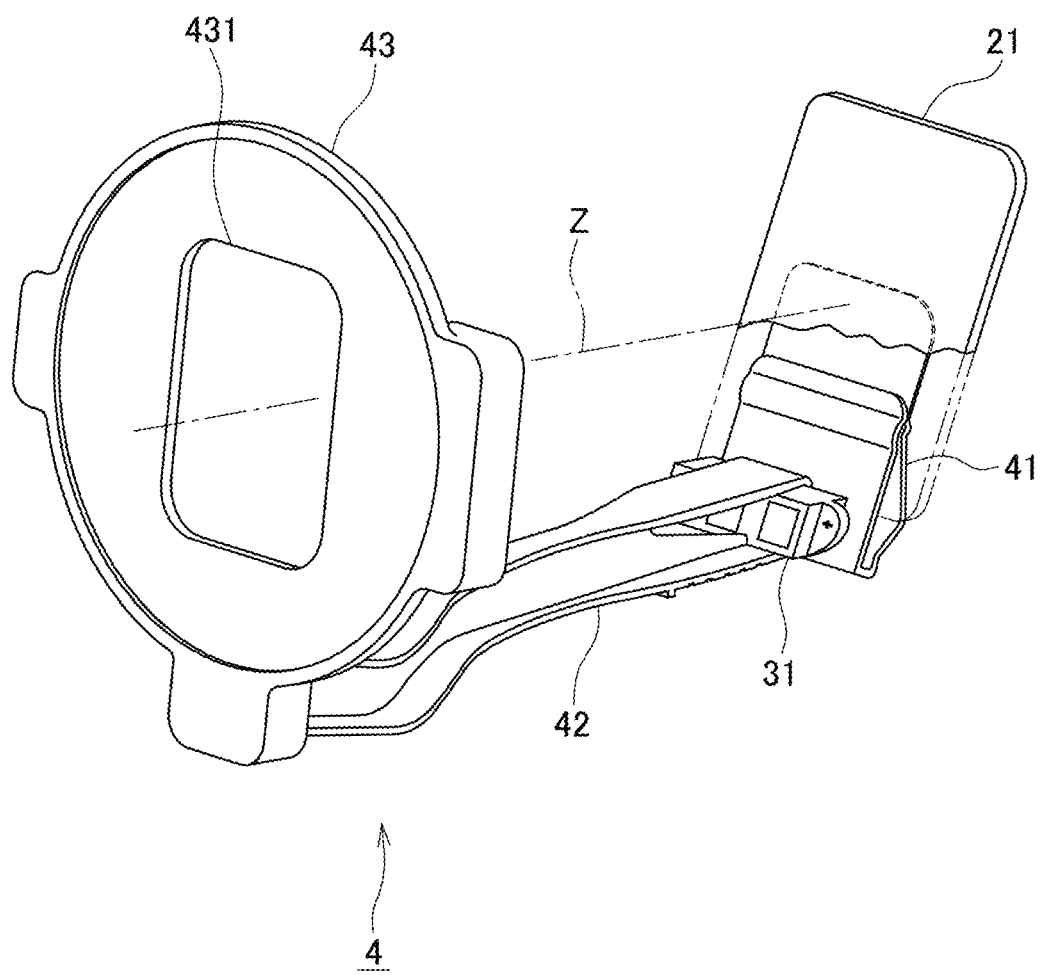

[FIG.4]
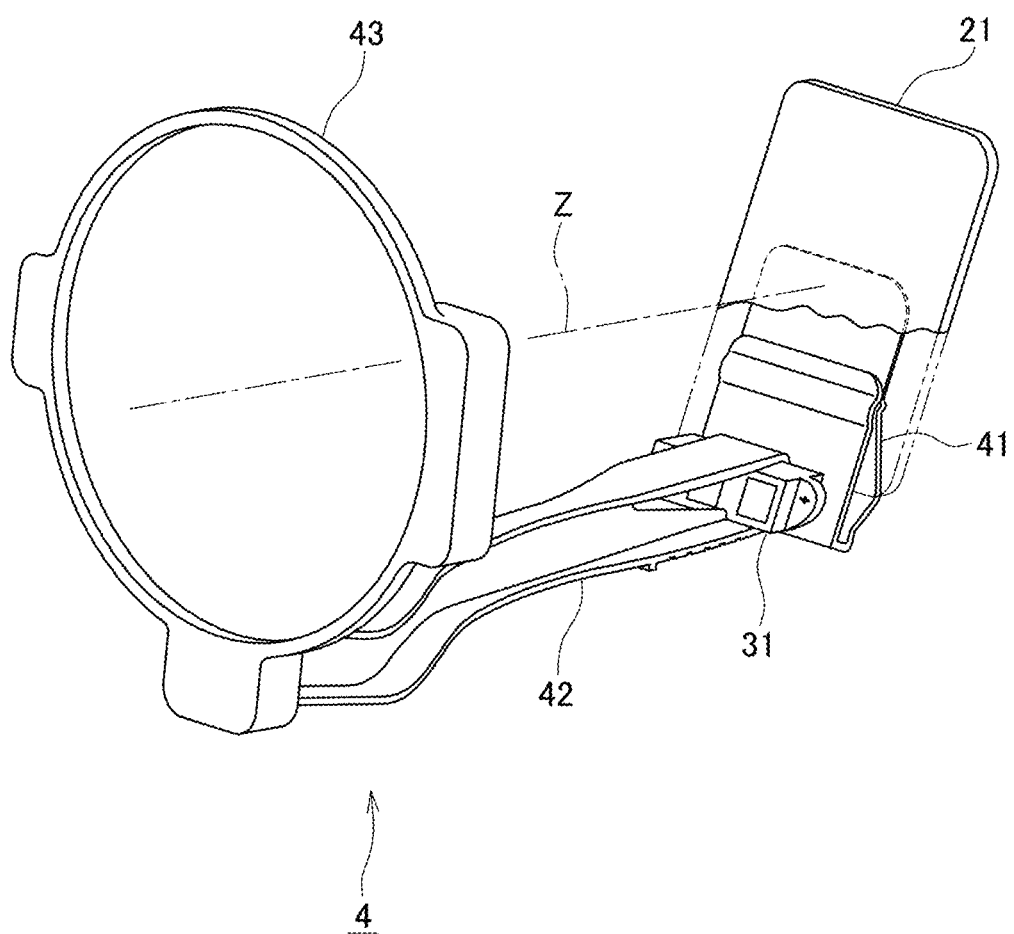

[FIG.5]
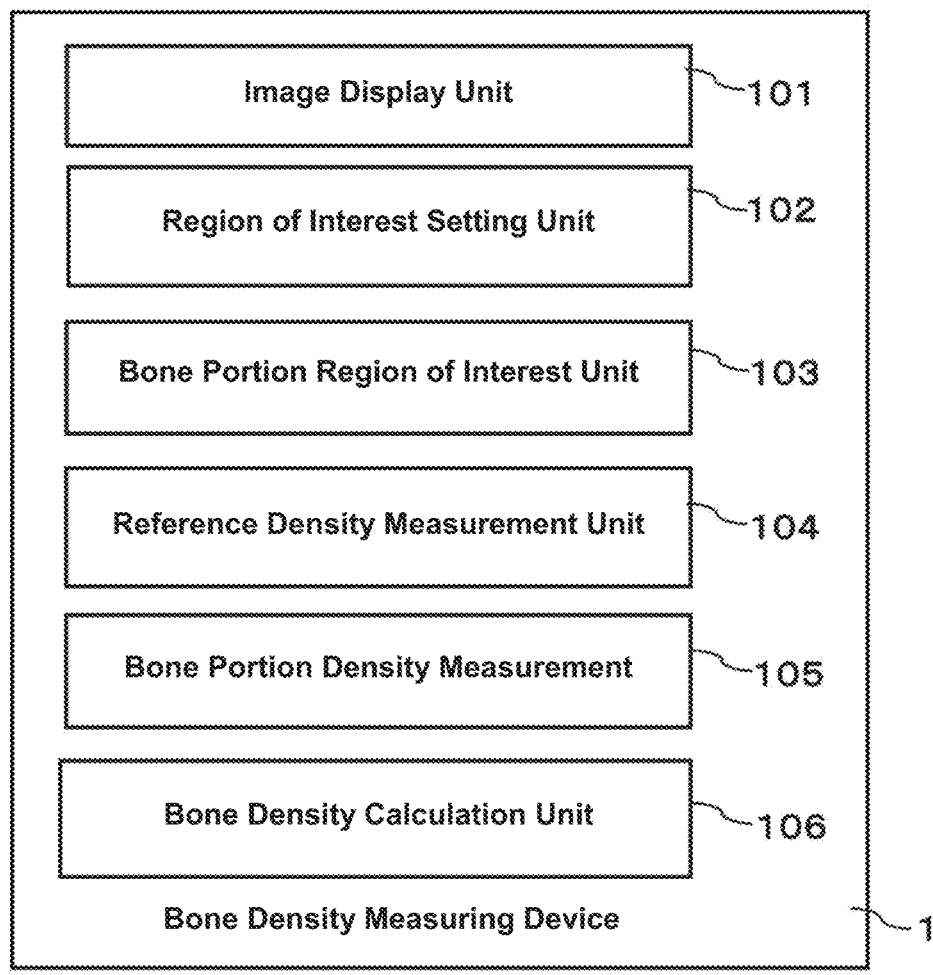

[FIG.6]

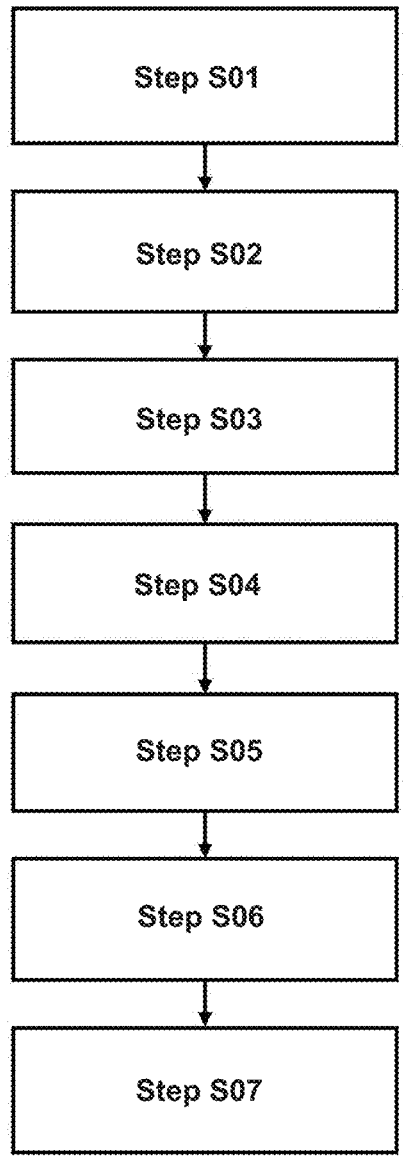

Step S01: Bone density measurement device delivers an instruction of a portion to be measured and of wearing the measurement aid.
Step S02: Imaging unit photographs the portion to be measured and captures the image on the imaging plate.
Step S03: Bone density measurement device receives the captured image, and image display unit displays the image.
Step S04: Density measurement unit for the reference measures the three densities in the reference.
Step S05: Setting unit for bone portion region of interest sets the bone region of interest.
Step S06: Density measurement unit for bone portion measures the bone density at its region of interest.
Step S07: Calculation unit for bone density calculates the bone density using the result of bone density measurement.

[FIG.7]
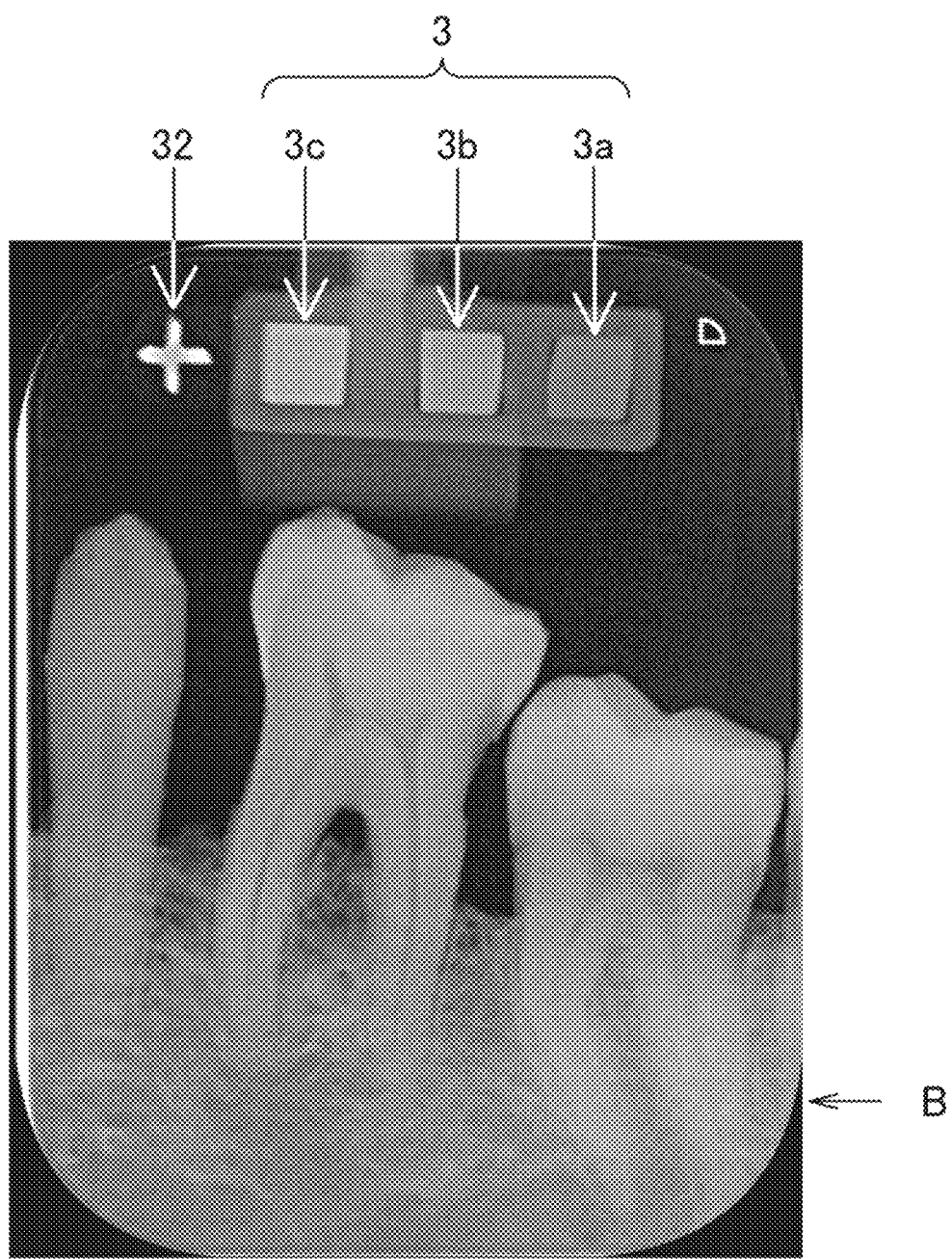

[FIG.8]
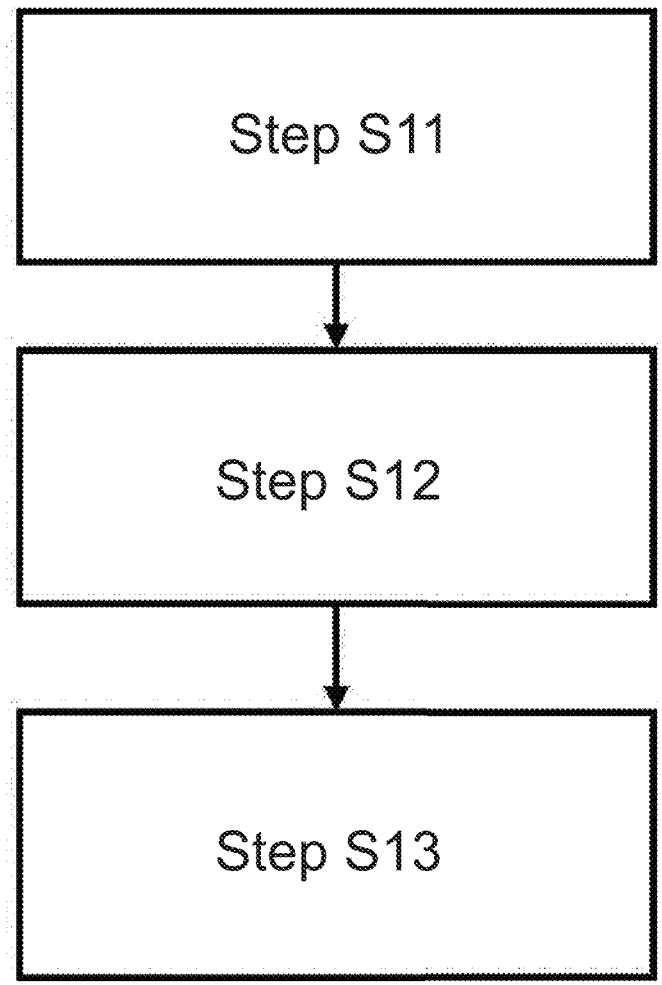
Step S11: Setting unit for the reference region of interest extracts the center coordinates of the marker.
Step S12: Setting unit for the reference region of interest extracts the center coordinates of the farthest reference sample.
Step S13: Setting unit for the reference region of interest sets the reference region of interest.

[FIG.9]
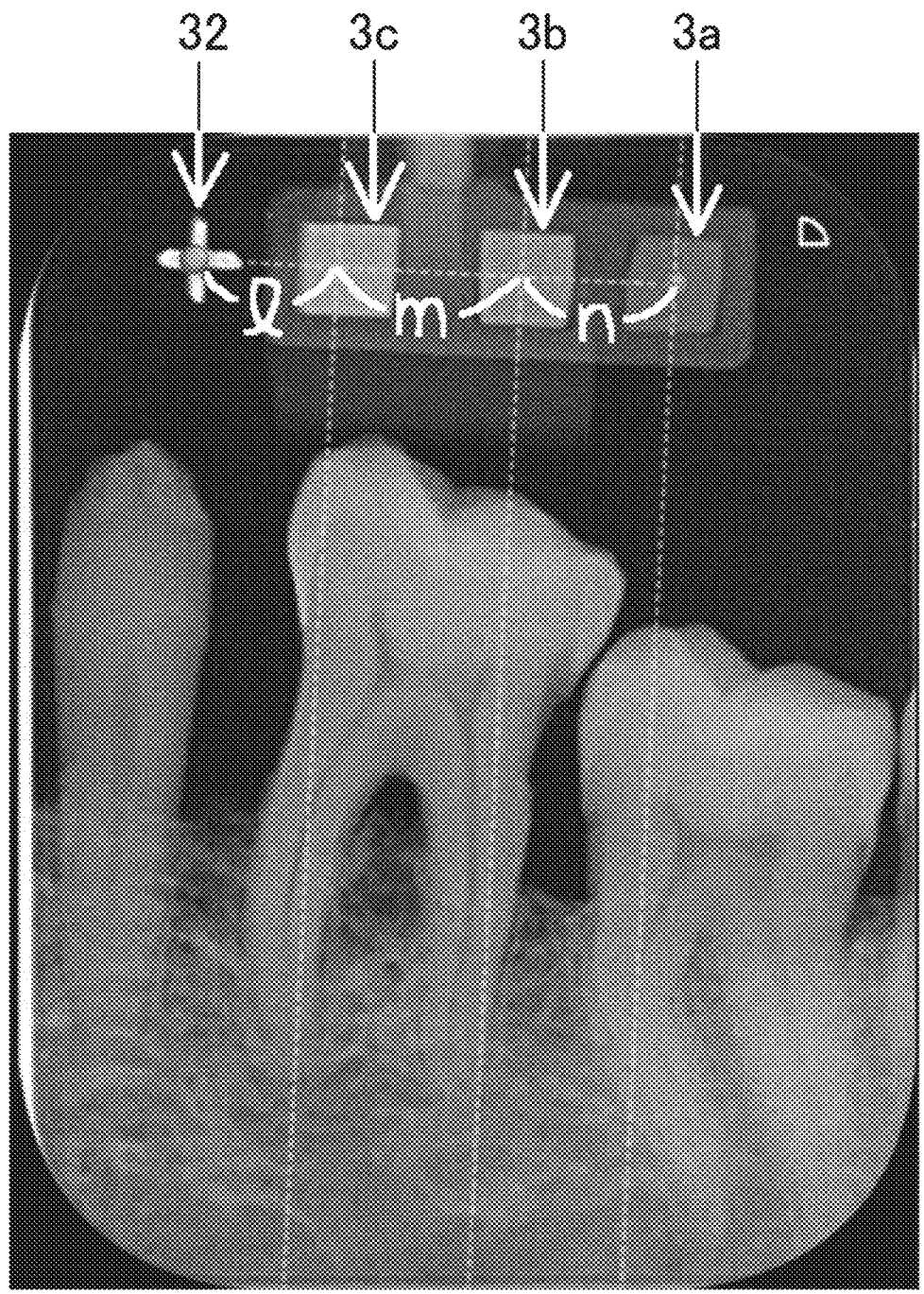

[FIG.10]
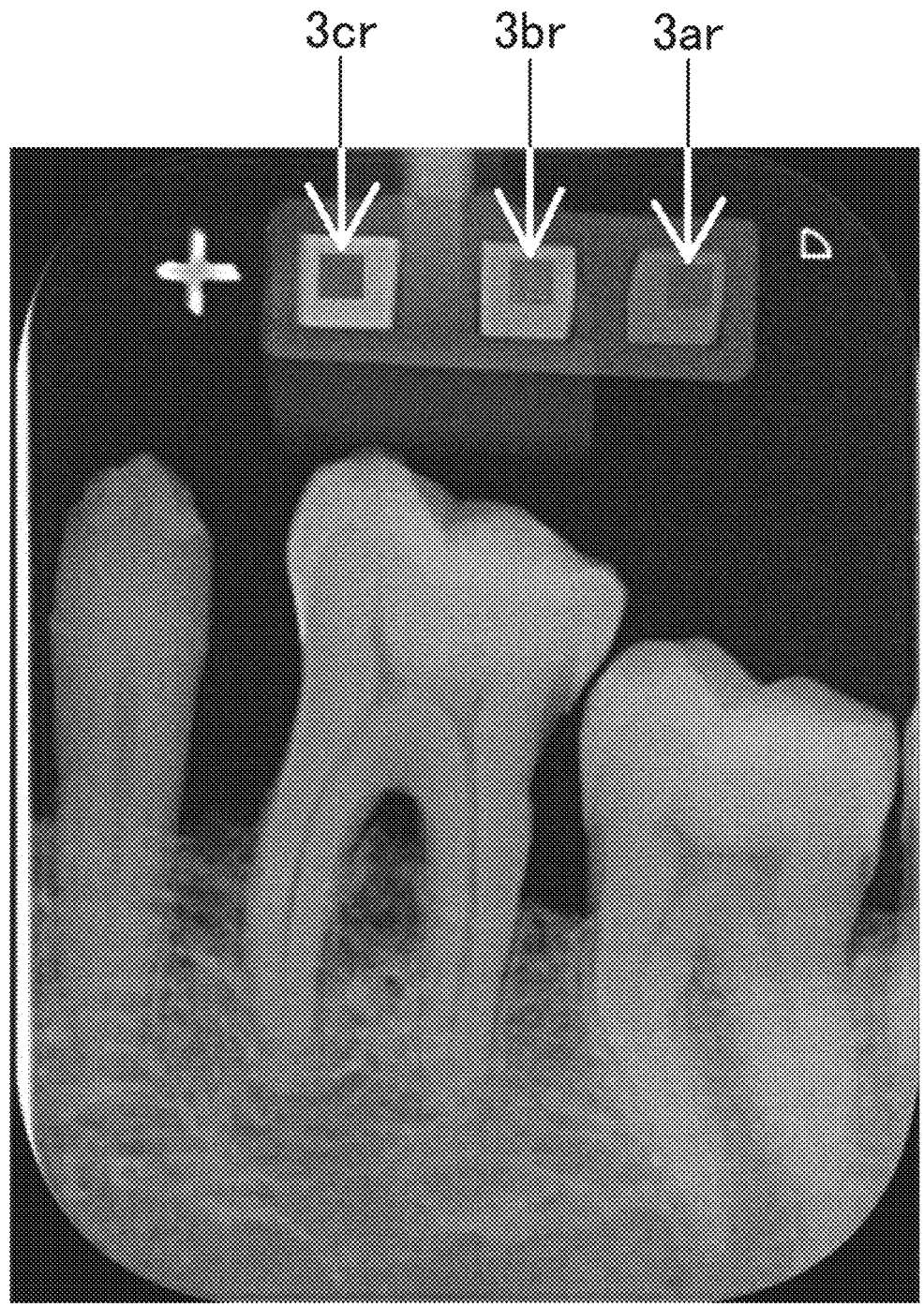

[FIG.11]
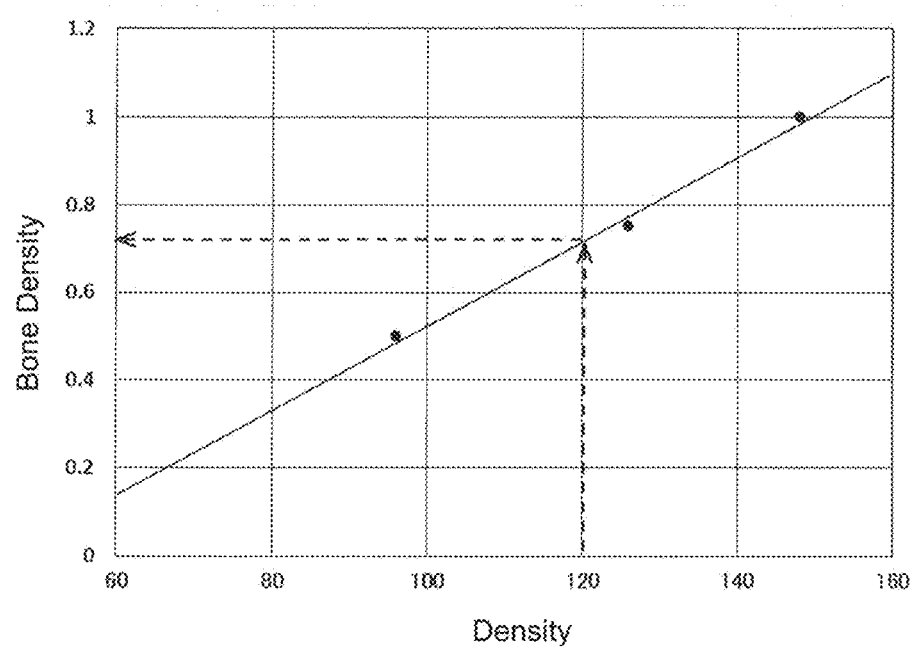

[FIG.12]
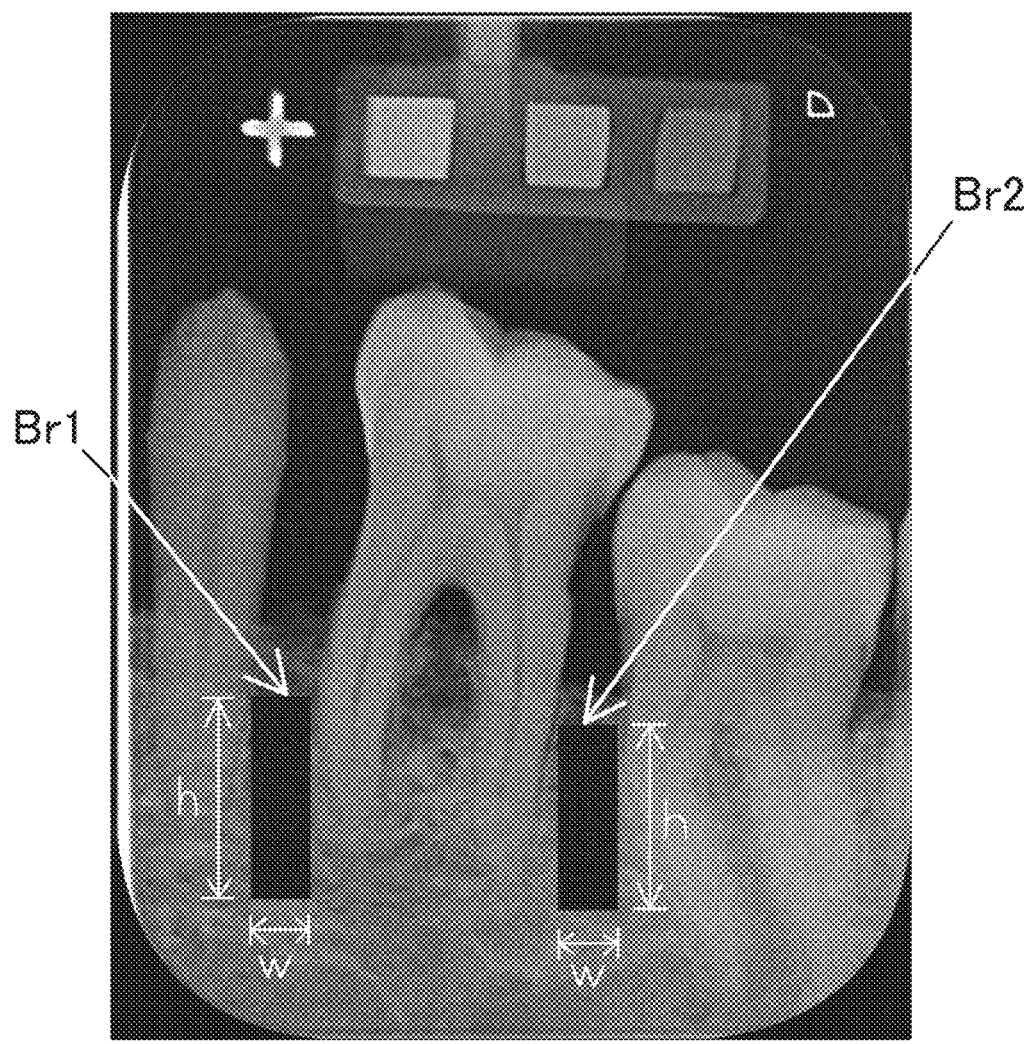

[FIG.13A]

[FIG.13B]
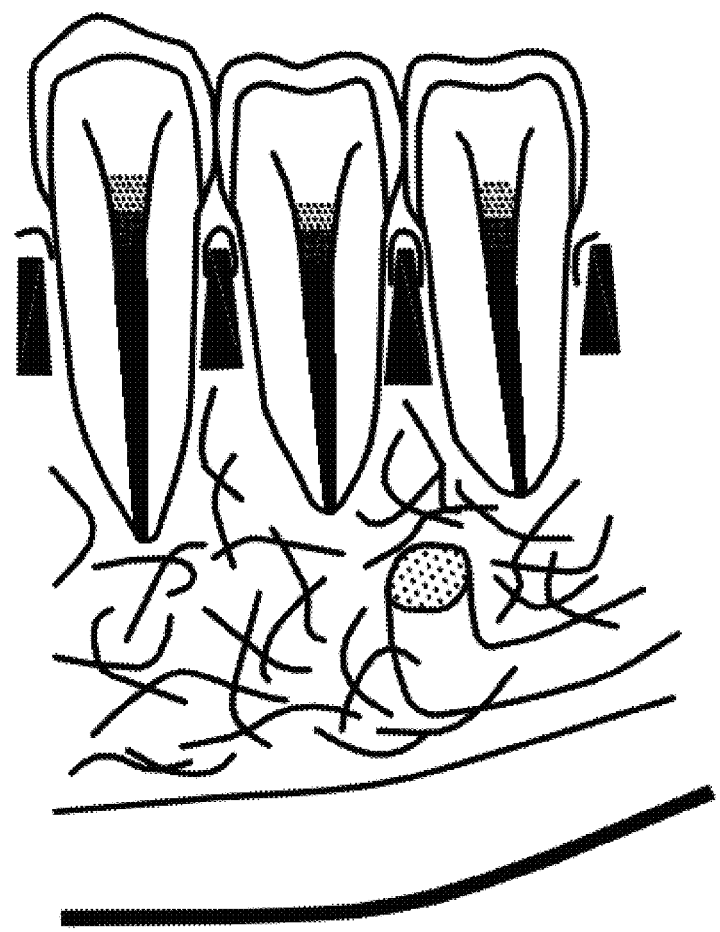

[FIG.13C]
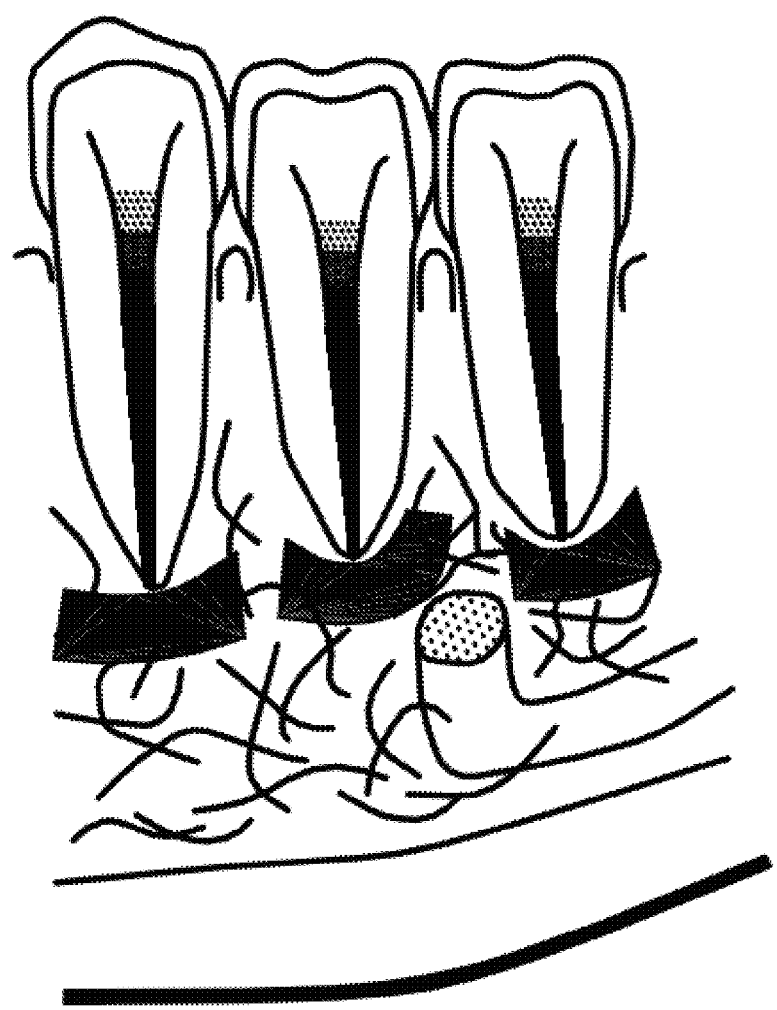

[FIG.13D]
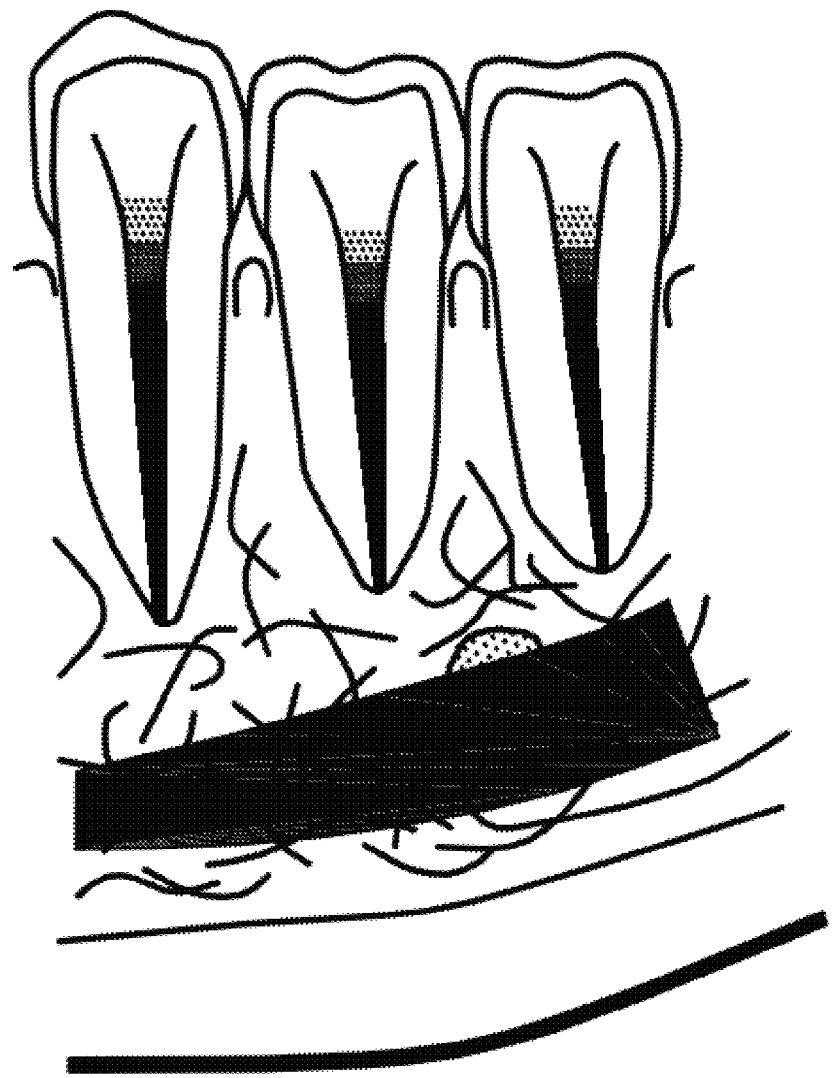

[FIG.13E]
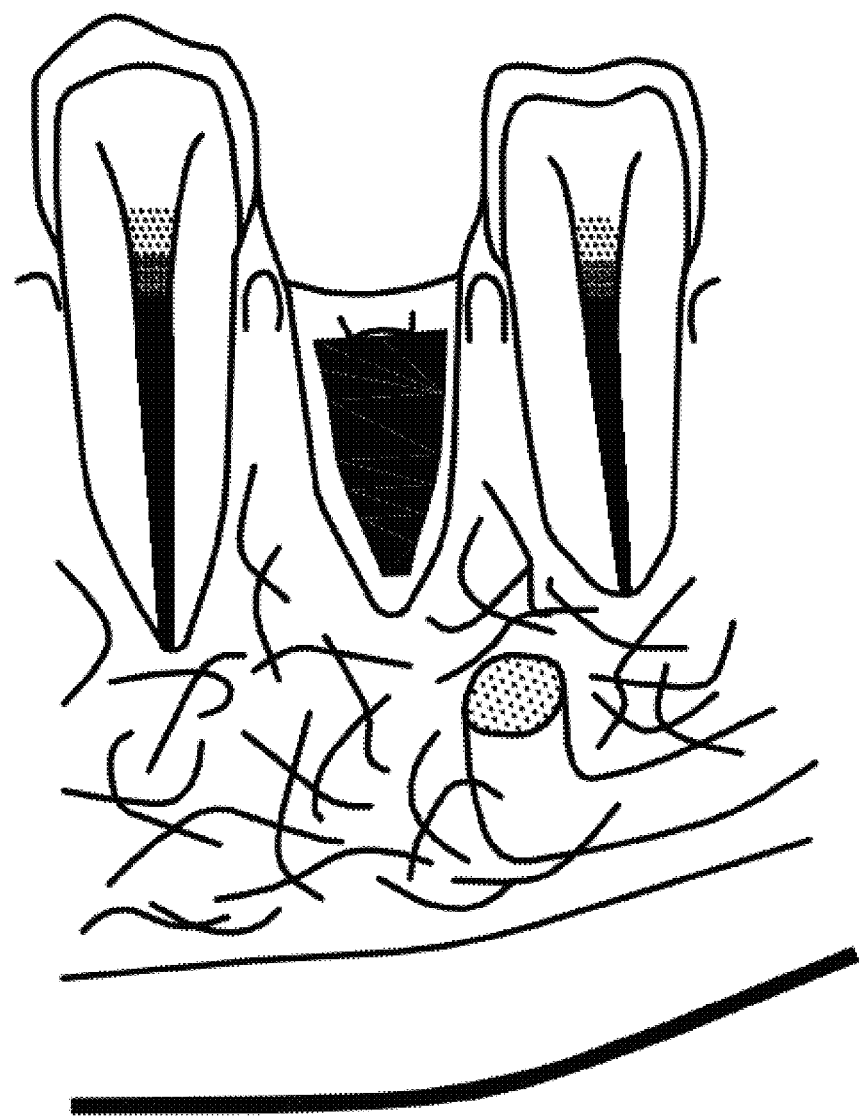

[FIG.13F]
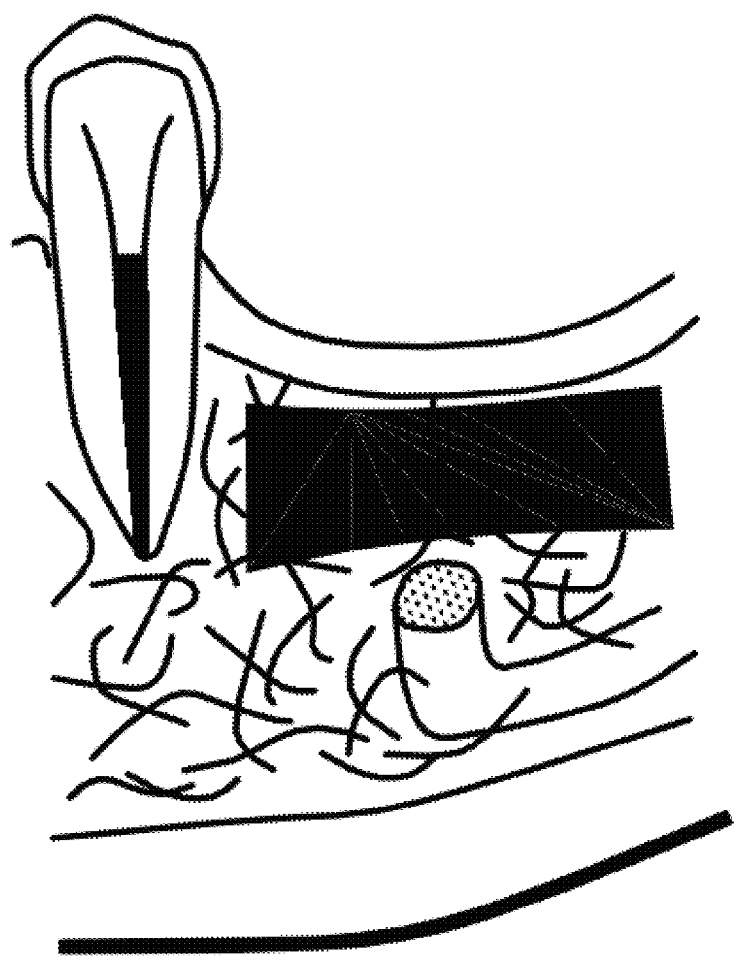

[FIG.14]
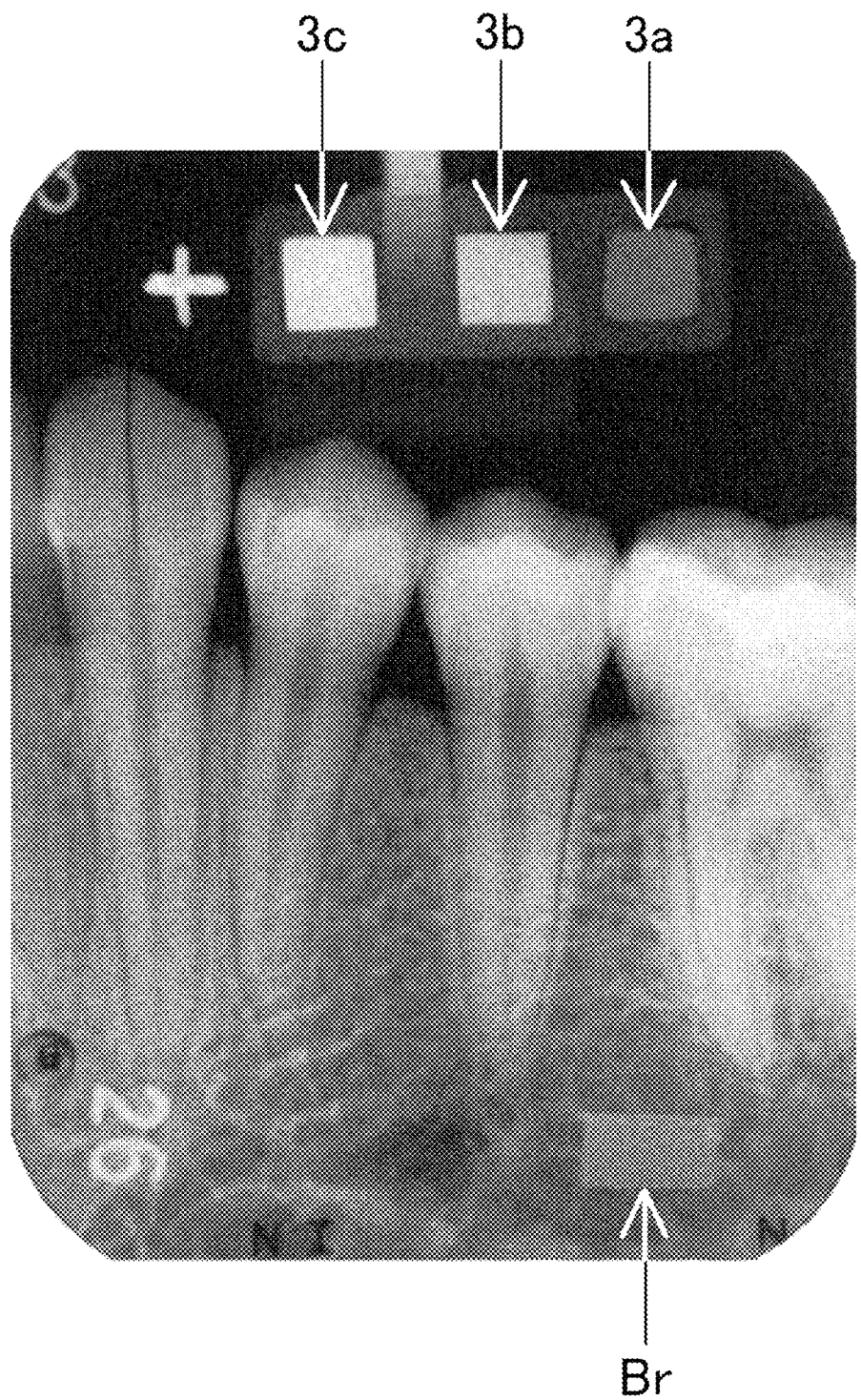

BONE DENSITY MEASUREMENT DEVICE, BONE DENSITY MEASUREMENT SYSTEM, AND IMAGING ASSISTING TOOL

CROSS REFERENCE TO RELATED APPLICATIONS

This application is a national stage application under 35 U.S.C. 371 of PCT Application No. PCT/JP2018/000357, filed on Jan. 10, 2018, which claims priority to JP Application No. 2017-002038, filed on Jan. 10, 2017. All of the above applications are incorporated herein by reference.

TECHNICAL FIELD

The present invention relates to an apparatus and system for measuring bone density using an X-ray image of a bone, and in particular, a bone density measurement device and a bone density measurement system for quantitatively calculating the bone density of alveolar bone from dental X-ray images. It also relates to an imaging assisting tool for the measurement.

BACKGROUND TECHNOLOGY

In the field of dental treatment, X-ray imaging is widely used at the time of treatment. In recent years, the bone density of alveolar is measured from photographed images, which is used for the treatment.

For example, Patent Document 1 discloses an technical idea, in which density pattern of alveolar bone by measuring the X-ray shadow density of alveolar bone is determined using aluminum standard substance, at least one index among alveolar hone width, resorbed area, and maximum absorbency is determined from the density pattern, and then the degree of bone atrophy of alveolar bone is evaluated by the index.

In this disclosure, indices such as alveolar bone width, resorbed area and maximum absorbency are used as a quantitative index of the degree of bone atrophy.

Further, Patent Document 2 discloses an technical idea of a bone density evaluation apparatus for evaluating bone density based on X-ray images of a mandible, especially an alveolar bone portion around a first premolar tooth, wherein the radiograph image contained an image of a specimen (aluminum block) placed alongside the mandible, and means for detecting the degree of shading of an image of a sample, for correcting the degree of shading of the radiographic images so that the detection result by the detection means coincided with the reference value, and for evaluating bone density based on the corrected degree of density corrected by the correction means were involved.

In this disclosure it was possible for example to quantitatively evaluate the bone density regardless of the difference in lightness and darkness of each X-ray image with respect to a plurality of image data captured on different days of the same patient.

Further, Patent Document 3 discloses a standard sample having a composition and compactness very close to the object to be measured such as teeth and bones of a human body and containing no impurities, and a method of manufacturing the same to be able to quantitatively calculate the density of the object to be measured such as teeth and bones of the human body and the amount of inorganic salt.

According to this disclosure, the composition desirable as a standard sample and its manufacturing method when quantitatively evaluating a bone density from a radiographic image are shown.

PRIOR ARTS

Patent Document

[Patent Document 1] Japanese Patent Laid-Open Application No, S62-266053.
[Patent Document 2] Japanese Patent No. 4077430.
[Patent Document 3] Japanese Patent No. 3300690.

SUMMARY OF THE INVENTION

Problems to be Solved by the Invention

In the bone atrophy degree evaluation method of Patent Document 1, however, there remained a problem that the evaluation result could not be regarded as universal, because it cannot be expressed by bone mass per unit area (g/square cm), a general expression method of bone density.

Also, in the bone density evaluation apparatus of Patent Document 2, there remained a problem that hone density was not expressed by a method of general hone density expression, in spite of the degree of the density for each image could be corrected and compared quantitatively in the disclosure.

It is desirable, however, to aim to apply aggressively the disclosure on the standard sample of Patent Document 3, in view of the effectiveness. In the present invention, a standard sample is expressed as a reference.

In addition, none of the patent documents has disclosed the effective imaging aid for imaging the reference and the measuring object, that is, the bone portion, particularly the alveolar bone portion, on the same screen.

Therefore, in order to solve the above-mentioned problems, it is an object of the present invention to provide a device and a system to calculate bone density quantitatively using the X-ray image of the photographed bone portion, particularly the alveolar bone, and to provide an aid for accurate and easy X-ray imaging of alveolar bone.

Means for Solving the Problems

To solve such problems, the present invention relates to A bone density measurement device, comprising:

An image display unit for displaying an X-ray image relating to a photographed bone portion and a reference body on identical screen;

A reference body density measurement unit configured to measure density of said X-ray image of the displayed reference body;

A bone portion density measurement unit configured to measure density of said X-ray image of the displayed bone portion; and A bone density calculation unit configured to calculate bone density of the bone portion by comparing the X-ray image density of the bone portion with the X-ray image density of the reference body.

In this way, accurate and universal results of bone density evaluation can be obtained, because the reference body concentration measurement unit and the bone portion density measurement unit measure densities (pixel values or gradations of the gray scale image) of the reference body and of the bone portion of interest, and then the bone density calculation unit can calculate the bone density as an absolute numerical value by comparing the densities.

Further, bone density measurement device of the present invention may be characterized in that the reference body has a composition close to that of a tooth.

In this way, the correlation of the image density between the reference body and the bone portion can be obtained more accurately, which enables obtaining bone density value with high accuracy.

Furthermore, the bone density measurement device of the present invention may be characterized in that the reference body is characterized in that a hydroxyapatite or a hydroxyapatite homolog in which hydroxyl group of the apatite is substituted with another element is mixed with carbon at different mixing ratios.

In this way, specifically the most suitable reference body can be gained, and in addition, the correlation becomes more accurate.

Furthermore, the bone density measurement device of the present invention may be characterized in that the reference body includes a sample from which three levels of image density can be obtained, and that the bone density calculation unit calculates bone density using them.

In this way, the processing in the photographing stage, the comparison stage, and the bone density calculation stage becomes simple because the number of stages of the reference body is reduced, whereas a large economic advantages are given because the practical accuracy is sufficiently maintained even in three steps as in the present invention.

Furthermore, the bone density measurement device of the present invention may be further characterized in that detection of the reference body is started by reading a marker attached to a case housing the reference body.

In this way, using the markers simplifies the device and the detection procedure and also provides accurate data.

Furthermore, the bone density measurement device of the present invention may be characterized in that the device further comprises a reference body region of interest setting unit configured to set a region of interest of the reference body after detection of the reference body is started.

In this way, even when the density of the reference body is not uniform, many pixels can be sampled to obtain a representative value average value, median value, mode value, etc.), so more accurate detection becomes possible.

Furthermore, another embodiment of the present invention is A bone density measurement system, comprising: a reference body for bone density measurement; a photographing device for simultaneously photographing an X-ray image of a bone portion and an X-ray image of the reference body; and a bone density measurement device as described above.

In this way, as a system including the bone density measurement device, the effect of the bone density measurement device can be sufficiently exhibited.

In addition, the reference body of the present invention may be characterized in that the reference body has a composition close to that of a tooth. In this way, as a system including the reference body and the bone density measurement device, the effect of the bone density measurement device can be sufficiently exhibited.

Furthermore, the bone density measurement system of the present invention can be characterized in that the reference body is characterized in that a hydroxyapatite or a hydroxyapatite homolog in which hydroxyl group of the apatite is substituted with another element is mixed with carbon at different mixing ratios. Also in this way, as a system including the reference body and the bone density measurement device, the effect of the bone density measurement device can be sufficiently exhibited.

The bone density measurement system of the present invention may also be characterized in that the reference body comprises a sample capable of obtaining three levels of image density. According to this, as a system including the reference body and the bone density measurement device, the effect of the bone density measurement device can be sufficiently exhibited.

Furthermore, the bone density measurement system of the present invention may be characterized in further comprising: a case for housing the reference body; and an auto-readable marker provided on the case. In this way, as a system including the reference body and the bone density measurement device, the effect of the bone density measurement device can be sufficiently exhibited by using the marker.

Furthermore, the bone density measurement system of the present invention may be characterized by having a photographing aid device configured to hold the reference body to simultaneously photograph the reference body and the bone portion.

In this way, X-ray imaging of the reference body and the alveolar bone can be performed accurately and easily, and the burden on the subject can be reduced, and highly accurate bone density measurement results can be obtained.

Further, yet another embodiment of the present invention is an imaging assisting tool, comprising: a holding portion configured to hold an image information detection medium for photographing a bone portion; and a support portion for supporting the holding portion at an appropriate position, the support portion provided on one side of the holding portion, wherein the photographing aid device comprises a mechanism configured to hold a reference body on the support portion side of the holding portion so as to be detected by the image information detection medium together with the bone portion.

In this way, as a photographing aid for holding a reference body simultaneously photographed with the bone for measuring bone density, it also becomes effective, even when it is used not only with the bone density measurement system of the present invention but also other with the bone density measurement systems of other than the present invention.

Effect of the Invention

In the bone density measuring device and the bone density measuring system according to the present invention, accurate and universal bone density values can be obtained, because the image comparing unit compares the region of interest with the reference by using an appropriate reference, and the bone density calculating unit further calculates the bone density in absolute value.

BRIEF DESCRIPTION OF THE DRAWINGS

FIG. 1 is a hardware configuration diagram of a bone density measuring system according to one embodiment of the present invention.

FIG. 2 is an illustration of a reference of a system according to one embodiment of the present invention.

FIG. 3 is an explanatory illustration of a imaging aid of a system according to one embodiment of the present invention.

FIG. 4 is an explanatory illustration of another imaging aid of the system according to one embodiment of the present invention.

FIG. 5 is a functional configuration diagram of a bone density measuring device according to one embodiment of the present invention.

FIG. 6 is an operation flow of a system according to one embodiment of the present invention.

FIG. 7 is an example of a captured image of a system according to one embodiment of the present invention.

FIG. 8 is an operation flow of setting a region of interest for the reference in a system according to one embodiment of the present invention.

FIG. 9 is an example of an image of a setting unit of a region of interest for the reference in a system according to one embodiment of the present invention.

FIG. 10 is an example of an image of a setting unit of a region of interest in the system according to one embodiment of the present invention.

FIG. 11 is a correlation diagram of image density and bone density of a system according to one embodiment of the present invention.

FIG. 12 is an explanatory illustration of a method for setting a region of interest of the device according to one embodiment of the present invention.

FIG. 13A is an explanatory view showing an example of a region of interest of a bone portion in the device according to one embodiment of the present invention.

FIG. 13B is an explanatory illustration showing an example of a region of interest of a bone portion in the device according to one embodiment of the present invention.

FIG. 13C is an explanatory illustration showing an example of a region of interest of a bone portion in the device according to one embodiment of the present invention.

FIG. 13D is an explanatory illustration showing an example of a region of interest of a bone portion in the device according to one embodiment of the present invention.

FIG. 13E is an explanatory illustration showing an example of a region of interest of a bone portion in the device according to one embodiment of the present invention.

FIG. 13F is an explanatory illustration showing an example of a region of interest of a bone portion in the device according to one embodiment of the present invention.

FIG. 14 is another example of a captured image of a system according to one embodiment of the present invention.

EMBODIMENTS OF THE INVENTION

Hereinafter, a bone density measuring system and a bone density measurement apparatus according to a first embodiment of the present invention are described with references to the drawings. In the following, the part necessary for the description to achieve the object of the present invention is schematically shown, the part necessary to describe the corresponding part of the present invention is mainly described, and omitted part is regard to be based on well-known technologies.

FIG. 1 is a hardware configuration illustrating a bone density measurement system 100 according to one embodiment of the present invention. The bone density measurement system 100 includes a bone density measurement device 1, an imaging device 2, a reference 3, and an imaging aid 4. Note that the imaging aid 4 may not be used depending on the situation, or different photographing aids may be used.

Here, the bone density measurement apparatus I may be one or plurality of personal computer, server, or dedicated device comprising a display unit 11 for displaying character and image information, an input unit 12 such as a keyboard for inputting information, an output unit 13 such as a printer for outputting information, storage unit 14 such as hard disk drives for storing information and programs, an interface unit 15 connected to the outside by wire and/or wireless, and a control unit 16 such as a CPU for controlling the whole system. These components may be integrally configured, or distributed as in cloud computing.

The imaging device 2 is a device for imaging a dental alveolar bone portion radiographically and the like. Although a dental X-ray imaging apparatus is suitable, it is not limited thereto, and a dental panoramic X-ray imaging apparatus, an X-ray imaging apparatus not limited to dental use, an imaging apparatus by MRI, CT, etc., an imaging apparatus by ultrasonic waves or a combination thereof may be applied. Depending on the images obtained, it may be possible to make an appropriate bone density measurement.

The imaging apparatus 2 includes an image information detection device provided apart from the apparatus main body. As the image information detection device, for example, an imaging plate 21 such as a plate where a photostimulable phosphor powder is coated on one side of an organic film is suitable, but it is not limited thereto. A film (X-ray film) or a solid semiconductor detector such as a flat panel detector (FPD) may be used as the image information detection device.

The reference 3 is disposed so as to be captured on the same screen when imaging a bone portion of the subject, in particular, an alveolar bone portion (outside of the configuration of the present invention). Here, it is preferable that the reference 3 has a composition close to that of the tooth, and more specifically, hydroxyapatite or a homolog of hydroxyapatite obtained by replacing the group of the apatite with another element, and carbon. More preferably, they are mixed at different mixing ratios.

FIG. 2 is an explanatory illustration of a portion related to the reference 3 of the bone density measurement system 100 according to one embodiment of the present invention. The reference 3 is composed of samples 3a, 3b and 3c from which three levels of image density are obtained. Here, the reference 3 is so configured that the correlation between values of bone density of each sample and the reference 3 are, for example, as follows:

reference 3a: mixing ratio 20% bone density, which corresponds to an equivalent value of 0.50 g/square cm, reference 3b: mixing ratio 60% bone density, which corresponds to an equivalent value of 0.75 g/square cm, and reference 3c: mixing ratio 100% bone density, which corresponds to an equivalent value of 1.00 g/square cm.

Here, the mixing ratio is the ratio of homologues of hydroxyapatite to the whole, which is also referred to as apatite equivalent. Practical accuracy is obtained with references of three-steps of densities. Of course, more detailed steps, four to five steps, for example, may be used, which makes handling more complicated, but can be expected to improve the accuracy.

Although the equivalent bone density value of the reference may be determined by a theoretical value calculated from the composition of the reference, it may be determined by imaging the reference along with a sample called "bone mineral determination phantom" or "bone density standard chart".

Although the approximate dimensions of the reference 3 are, for example, squares having an edge of 5 mm on a side facing to the imaging device 2 and a depth of about 10 mm, dimensions are not limited to these, and the thickness may be similar to that of a hard tissue such as a bone to be measured, because expression in g/square cm is commonly used. For example, it may be 8 mm for the lower front teeth, 10 mm for the premolars, and 12 mm for the molars.

Further, the reference 3 is inserted into and accommodated in the hole provided in the case 31, and the case 31 is provided with an automatic readable marker 32 formed in the form of a short cross in the direction perpendicular to the reference 3 in the direction of the reference 3 with a copper metal wire for example. Further, the position, shape of the marker are not limited to those shown in the figure as long as automatic reading is easy, and the insertion direction of the reference 3 is not limited to the side from the marker 32, and they can be from the opposite side, the top, or the bottom.

Furthermore, two protrusions 33 are provided on the top surface of the case 31. This is for positioning and fixing at the time of assembly.

The approximate dimensions of the case 31 are preferably, but not limited to for example, about 7 mm×24 mm on the side facing to the imaging device 2 with a depth of about 10 mm. It is not always necessary for the reference to be accommodated in the case 31. Automatic reading may be realized using the position of the image, the shape of the reference, etc. without the marker 32, or it can be realized by the operator of the apparatus using an input unit such as a mouse.

FIG. 3 and. FIG. 4 are explanatory illustration of the imaging aid 4 of the bone density measurement system 100 according to the embodiment of the present invention. Here, the imaging aid 4 holds the reference 3 in order to simultaneously photograph the reference 3 and the alveolar bone portion B, and the reference 3 is accommodated in the case 31 to which the marker 32 is attached. However, it is not necessary to be housed in the case 31, and when the case 31 is not used, for example, the reference 3 may be fixed to the imaging aid 4 to be held.

The imaging aid 4 comprises a holding portion 41 for holding the planar imaging plate 21 for capturing an X-ray image so as to be substantially orthogonal to the imaging main axis Z of the main body of the imaging device 2, an elongated rod-like support portion 42 provided at one end of the holding portion 41 so as to be substantially orthogonal to the holding portion 41 and for supporting the holding portion 41 in an appropriate position by engaging the upper and lower teeth with each other, and an annular direction indication guide 43 provided on the opposite side of the holding portion 41 of the support portion 42 for facilitating imaging, wherein in particular, in FIG. 3, the space is provided at the center of the direction indication guide 43, and has a rectangular aperture 431 for an image to be rectangular.

Note that FIG. 4 does not have the rectangular stop 431 and the inside of the direction indication guide 43 is large in space, and such a simple structure may be used if it is not necessary to narrow it to the rectangular shape. Furthermore, the direction indication guide 43 may not necessarily be provided depending on the imaging method and the like.

Furthermore, the case 31 accommodating the reference 3 is installed at the end of the support portion 42 on the holding portion 41 side so as to be detected by the imaging plate 21 together with the alveolar bone portion.

Specifically, the case 31 containing the reference 3 is inserted into a substantially U-shaped space formed at the end of the support unit 42 on the side of the holding unit 41, and the two projections 33 provided on the case 31 side are fixed by fitting it into the groove on the side of the support portion 42, which is not shown.

Here, the installation position and the fixing method of the case 31 accommodating the reference 3 are not limited to the above description, and may be installed in the holding unit 41, and the known method such as screwing may be used as the fixing method or alternatively, the reference 3 and the marker 32 may be fixed to the support unit 42 or the holding unit 41 without using the case 31.

The imaging aid 4 may be used for imaging bone portions other than alveolar bone portions. In that case, the shapes of the holder 4 for holding the imaging plate 21 and the case 31 containing the reference 3 or the reference 3 itself and the support 42 for properly supporting the holder 41 is designed according to the imaging portion, and in short, it may be able enough to capture the bone portion and the reference 3 on the same screen.

FIG. 5 is a functional configuration diagram of a bone density measurement unit 1 according to one embodiment of the present invention. The bone density measuring device I has an image display unit 101 which displays an X-ray image of a photographed bone portion such as alveolar bone and a reference for measuring bone density on the same screen, region of interest setting unit 102 for the displayed reference image, reference density measurement unit 103 which measures the concentration of the set region of interest for the reference, region of interest setting unit 104 for setting a region of interest in the displayed image of a bone portion such as alveolar bone, a bone concentration measurement unit 105 for measuring the concentration of the bone region of interest, and bone density calculation unit 106 and the like, for calculating the bone density in region of interest of the bone portion by comparing the image density of the bone with that of the reference, as functional elements for the hardware components mentioned above to realize functions cooperatively.

The operations of the bone density measurement system and the bone density measurement unit of these configurations are described.

FIG. 6 is an operation flow of a bone density measurement system 100 according to one embodiment of the present invention. The bone density measurement apparatus 1 indicates the region to be measured on the subject whose bone density is to be measured via the display unit 11, and instructs to attach the imaging aid 4 (step S01). Specifically, in the case of the maxillary teeth, the tip portion (tooth top portion) of the tooth to be imaged is placed on the case 31 storing the reference 3, and occlusal portion 42 is engaged with and fixed to the subject such that the holding portion 41 holding the imaging plate 21 is directed toward the root direction (upward) inside the target tooth.

In case for the lower teeth, the holding portion 41 is placed upside-down.

Next, the imaging device 2 is fixed with its leading portion abutting on the direction indication guide 43, a picture is taken by the intraoral method so that the reference 3 and the alveolar bone part enter the same screen, and an image is captured on the imaging plate 21 (step S02).

Next, the bone density measurement device 1 receives the photographed image information via the main body of the imaging device 2 from imaging plate, or alternatively by reading the imaging plate 21 directly by the input unit 12 of the bone density measurement device 1, and the photographed image is displayed on the screen by bone density measuring the image display unit 101 (step 503).

FIG. 7 shows an example of a photographed image of the bone density measurement system according to an embodiment of the present invention, where the image display unit 101 of the bone density measurement device 1 displays the image of the alveolar bone portion B in the lower part, with the reference on the upper part of the screen. Here, in the image of the reference 3, the images of the reference samples 3a, 3b and 3c from which the image density of three levels are obtained sequentially from the left in the figure and the image of the marker 32 for automatic measurement are displayed.

In the drawing, the marker 32 and the reference 3 are not aligned in the horizontal direction, and are photographed slightly inclined. There are various situations in taking photographs, and a method that can accurately grasp the reference 3 is required even in a situation where they shift from the horizontal direction, which often occurs.

For that purpose, the region of interest reference setting unit 102 for the reference sets a region of interest for the reference. FIG. 8 is an operation flow for setting a reference region of interest for the reference in the hone density measurement system according to an embodiment of the present invention.

First, center coordinates of the marker 32 are extracted on the image (step S11). Specifically, using the fact that the image of the marker 32 is a relatively thin line and having high luminance, only the image of the marker 32 is determined by a method such as gray scale OPENING processing, image difference processing, etc., and its center coordinates (Position) is extracted. In addition, extraction of the center coordinates of the marker 32 is not limited to the method, and may be searched by pattern matching, for example.

Next, the center coordinates of the farthest reference sample 3a are determined by using the center coordinates of the marker 32 (step S12). Specifically, the center coordinates is determined by the position of the distance on the screen corresponding to the furthest distance to the reference 3c on the screen, which was previously set, by extending edge of marker 32 in the substantially horizontal direction. FIG. 9 is an example of an image related to the reference region of interest setting unit for the reference in the bone density measurement system according to one embodiment of the present invention, in which the center coordinates of the marker 32 and the center coordinates of the farthest reference sample 3a are shown.

Next, the region of interest of the reference is determined using the center coordinates of the marker 32 and the center coordinates of the farthest reference sample 3a (step S13). Specifically, as shown in FIG. 9, the distance between the center coordinates of the marker 32 and the center coordinates of the farthest reference sample 3a is divided by a predetermined ratio (1:n, for example, as shown in the figure), and then, the center coordinates of the other reference samples 3c, 3b are determined.

FIG. 10 is an example of an image related to a reference region of interest setting unit of the bone density measurement system according to an embodiment of the present invention, showing a state in which the region of interest is set. Since the image of the reference 3 is often photographed tilted from the horizontal direction as described above, and a correction is necessary because there are subtle errors due to the influence of the X-ray incident angle and so on, the image reference is confirmed from the relative value of the distance to the references 3a, 3b, and 3c, and in addition, a method in which the region of interest is created with a coefficient that minimizes the variance of the concentration in the region of interest.

Thereafter, areas of a predetermined number of pixels in the vertical and horizontal directions are set from the center coordinates of the reference samples 3a, 3b, and 3c. These are the reference regions of interest 3ar, 3br, and 3cr. Here, the sizes of each of the reference regions of interest 3ar, 3br, and 3cr are squares with one edge length of 30 pixels.

By the before-mentioned methods, the region of interest of the reference can be automatically and accurately determined without human intervention, giving a large effect.

Of course, reference in the image shown in FIG. 9 may be presented on the screen to prompt the operator for input, even if the region of interest of the reference can not be automatically determined by some reason.

Next, the reference density measurement unit 103 measures the image density of the reference samples 3a, 3b, and 3c from the image of the region of interest of the reference 3 by a known method (Step S04 in FIG. 6). Here, any of average value, median value, and mode value can be set as a representative value of density according to the situation.

For example, since it is preferable to use the central value as the representative value of the density as for the concentrations of the reference bodies 3a, 3b and 3c, it is desirable to use an average value or median value, and especially the average value is the most desirable when the density distribution is stable. On the other hand, in the case of a density distribution in which only a portion is peaked as shown in the marker 32, it is preferable to use the mode as the representative value of the density.

FIG. 11 is a diagram showing the correlation between densities of images of the reference and the bone density in one embodiment of the present invention. Results of measurements in the above-mentioned example are shown as follows:

density=96 for the reference 3a, density=135 for the reference 3b, density=152 for the reference 3c.

Here, since the densities at the reference 3b and the reference 3c become excessively high because of the overlapping with the holding portion 41 or the support portion 42 of the imaging aid 4, they are corrected as follows:

density=96 for the reference 3a (no correction), reference density=135×0.93=126 for the reference 3b, density=152×0.97=148 for the reference 3c. As a result, the relationship between image densities and bone densities mentioned above is as follows:

bone density equivalent value=0.50 g/square cm for reference density 96 of the reference 3a, bone density equivalent value=0.75 g/square cm for density 126 of the reference 3b, bone density equivalent value−1.00 g/square cm for density 148 of the reference 3c.

These are illustrated in FIG. 12, from which a substantially linear correlation is observed.

This relation is expressed by an linear regression line of y=0.0095x−0.427, where x and y are image density and bone density, respectively.

Next, the bone portion region of interest setting unit 104 sets a bone portion, in particular, a region of interest Br of the alveolar bone portion (step S05 in FIG. 6). FIG. 12 is an explanatory view showing a method of setting a bone region of interest in the bone density measuring device according to one embodiment of the present invention, where two bone regions of interest Br1 and Br2 are set with the width w and the height h at positions approximately equidistantly spaced on either side of the tooth axis of a specific tooth. Further, the specifying the teeth and the area may be appropriately determined according to the application of bone density measurement.

Here, different hone region of interest may be set as a region of interest. FIGS. 13A to 13F are explanatory views showing an example of a bone region of interest in a bone density measurement device according to an embodiment of the present invention, wherein the black parts indicate the bone region of interest and in addition to the alveolar bone portion (FIG. 13A) described above, the alveolar crest (FIG. 13B), the apical portion. (FIG. 13C), the jaw bone body (FIG. 13D), the extraction socket (FIG. 13E), the jaw ridge (part to be treated by implants, technicians, etc.) (FIG. 13F), etc. may be selected besides the bone body portion, and the predetermined distance and dimensions may be selected as appropriate.

Here, FIG. 13E and FIG. 13F, in particular, are useful for the dentist to evaluate progresses of treatment and make a plan for the treatment, and the others are particularly useful for diagnosis support of periodontal disease, which is based on the quantitative evaluation of alveolar bone resorption.

As for the region of interest of the bone portion, the region may not necessarily be set, and a specific portion may be designated to measure the density at that portion.

Next, the bone portion density measurement unit 105 measures the density of the bone portion, in particular, the region of interest in the alveolar bone portion (step S06 in FIG. 6). For example, a representative value of the density is determined for the bone region of interest in the alveolar bone portion described above. The region of interest of the alveolar bone portion can be a region of interest that simultaneously includes a tooth region and a non-tooth region because the user can arbitrarily select it. In such a case, after observing the density distribution, the representative value is set to one of an average value, a median value, and a mode value. Here, it is assumed that, for example, the density is determined to be 120 as a representative value.

Although it is preferable to obtain the density as a representative value for the region of interest from the viewpoint of guaranteeing the accuracy, the density may be obtained by other methods such as the density of only a specific part. In some cases, it can be measured simply.

Next, the bone density calculation unit 106 calculates the bone density of the alveolar bone from the correlation between the density of the reference and the bone density and the density of the region of interest in the alveolar hone (step S07 in FIG. 6). In this case, the bone density at the concentration 120 is calculated to be about 0.71 g/square cm by using the approximate formula of FIG. 11. In this way, the bone density of the alveolar bone portion can be obtained in g/square cm, a general-purpose unit.

Note that the relationship between the reference density and the bone density described above is different for each photographed image. While FIG. 14 is an example of a film image, which is not a digital image and in this case the density (pixel value) is significantly reduced, the bone density can be appropriately calculated by creating a correlation diagram as shown in FIG. 11, because all the reference regions of interest 3a, 3b, 3c and the bone portion of interest Br are similarly reduced.

INDUSTRIAL APPLICABILITY

The present application has a broad industrial applicability in that it can measure bone density using dental x-ray images, and can be used to support the diagnosis of osteoporosis and the like.

DESCRIPTION OF THE CODE

1 Bone density measurement device
2 Shooting device
3 Reference
4 imaging aids
100 Bone density measurement system

The invention claimed is:
1. A bone density measurement device, comprising:
an image display unit for displaying an X-ray image relating to a photographed bone portion and a plurality of reference bodies, whose equivalent values of bone density each are given, on identical screen;
a reference body density measurement unit configured to measure density of said X-ray image of the displayed plurality of reference bodies;
a bone portion density measurement unit configured to measure density of said X-ray image of the displayed bone portion;
a reference body region of interest setting unit configured to set a region of interest of the plurality of reference bodies; and
a bone density calculation unit configured to calculate bone density of the bone portion by gaining a relation between the plurality of X-ray image density of the plurality of reference bodies and each corresponding bone density, by making an amendment to the relation to obtain an amended relation expressed by a linear regression line between the plurality of X-ray image density of the plurality of reference bodies and each corresponding bone density, and by referring to the amended relation expressed by the linear regression line and the X-ray image density of the bone portion,
wherein a case in which the reference bodies are accommodated is provided with a marker, wherein, in said reference body region of interest setting unit, a center coordinate of said marker is extracted, center coordinates of the farthest of said reference bodies are determined by using said center coordinate of said marker, center coordinates of the rest of said reference bodies are determined by using said center coordinate of said marker and said center coordinates of the farthest of said reference bodies, wherein areas of a predetermined number of pixels in vertical and horizontal directions are set from said center coordinates of said reference bodies to set said region of interest of the reference bodies, and wherein said reference body density measurement unit measures the density of said X-ray image of said region of interest of the reference body set by said reference body region of interest setting unit.
2. The bone density measurement device according to claim 1, wherein each of the plurality of reference bodies has a composition close to that of a tooth.
3. The bone density measurement device according to claim 2, wherein each of the plurality of reference bodies is characterized in that a hydroxyapatite or a hydroxyapatite homolog in which hydroxyl group of the apatite is substituted with another element is mixed with carbon at different mixing ratios.

4. The bone density measurement device according to claim 1, wherein each of the plurality of reference bodies includes a sample from which three levels of image density can be obtained, and wherein the bone density calculation unit calculates bone density using the three levels of image density.

5. A bone density measurement system, comprising:
a plurality of reference bodies for bone density measurement;
a photographing device for simultaneously photographing an X-ray image of a bone portion and an X-ray image of the plurality of reference bodies; and
a bone density measurement device,
wherein the bone density measurement device comprises:
an image display unit configured to display the photographed X-ray image of the bone portion and the photographed X-ray image of the plurality of reference bodies, whose equivalent values of bone density each are given, on identical screen;
a reference body concentration measurement unit configured to measure a density of the displayed X-ray image of the plurality of reference bodies;
a bone density measurement unit configured to measure a density of the displayed X-ray image of the bone portion;
a reference body region of interest setting unit configured to set a region of interest of the plurality of reference bodies; and
a bone density calculation unit configured to calculate bone density of the bone portion by gaining a relation between the plurality of X-ray image density of the plurality of reference bodies and each corresponding bone density, by making an amendment to the relation to obtain an amended relation expressed by a linear regression line between the plurality of X-ray image density of the plurality of reference bodies and each corresponding bone density, and by referring to the amended relation expressed by the linear regression line and the X-ray image density of the bone portion,
wherein a case in which the reference bodies are accommodated is provided with a marker, wherein, in said reference body region of interest setting unit, a center coordinate of said marker is extracted, center coordinates of the farthest of said reference bodies are determined by using said center coordinate of said marker, center coordinates of the rest of said reference bodies are determined by using said center coordinate of said marker and said center coordinates of the farthest of said reference bodies, wherein areas of a predetermined number of pixels in vertical and horizontal directions are set from said center coordinates of said reference bodies to set said region of interest of the reference bodies, and wherein said reference body concentration measurement unit measures the density of said X-ray image of said region of interest of the reference body set by said reference body region of interest setting unit.

6. The bone density measurement system according to claim 5, wherein each of the plurality of reference bodies has a composition close to that of a tooth.

7. The bone density measurement system according to claim 6, wherein each of the plurality of reference bodies is characterized in that a hydroxyapatite or a hydroxyapatite homolog in which hydroxyl group of the apatite is substituted with another element is mixed with carbon at different mixing ratios.

8. The bone density measurement system according to claim 5, wherein each of the plurality of reference bodies comprises a sample capable of obtaining three levels of image density.

9. The bone density measurement system according to claim 5, further comprising:
a case for housing the plurality of reference bodies; and
an auto-readable marker provided on the case.

10. The bone density measurement system according to claim 5, further comprising a photographing aid device configured to hold the plurality of reference bodies to simultaneously photograph the plurality of reference bodies and the bone portion.

* * * * *